Figure 1:
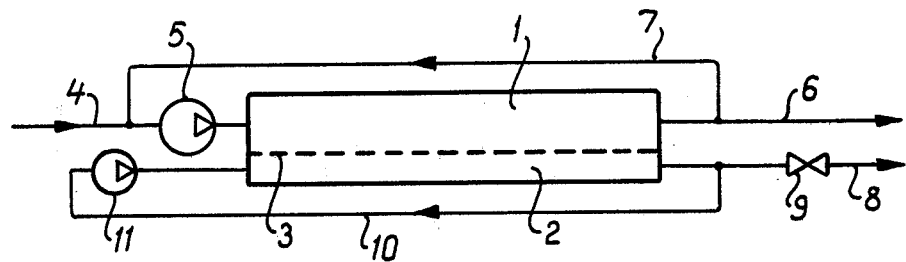

United States Patent [19]

Sandblom

[11] 4,105,547
[45] Aug. 8, 1978

[54] FILTERING PROCESS

[75] Inventor: Robert Mauritz Sandblom, Farsta, Sweden

[73] Assignee: Alfa-Laval AB, Tumba, Sweden

[21] Appl. No.: 641,769

[22] Filed: Dec. 17, 1975

[30] Foreign Application Priority Data

Dec. 23, 1974 [SE] Sweden ............... 7416257

[51] Int. Cl.² ............... B01D 13/00; B01D 31/00
[52] U.S. Cl. ............... 210/22 R; 210/23 F; 210/321 R; 210/349
[58] Field of Search ............... 210/321, 137, 349, 22, 210/23 F

[56] References Cited

U.S. PATENT DOCUMENTS

| | | | |
|---|---|---|---|
| 2,544,289 | 3/1951 | Andrews | 210/349 |
| 3,228,877 | 1/1966 | Mahon | 210/22 |
| 3,442,389 | 5/1969 | Mendelson | 210/321 A |
| 3,487,932 | 1/1970 | Forrester et al. | 210/137 X |
| 3,990,973 | 11/1976 | Boag et al. | 210/87 |

*Primary Examiner*—Charles N. Hart
*Assistant Examiner*—David R. Sadowski
*Attorney, Agent, or Firm*—Cyrus S. Hapgood

[57] ABSTRACT

A filterable fluid flows under pressure through a filtering passage along one side of the filter, so that there is a substantial pressure drop along the filter area in the flow direction. A fluid flow in this same direction is provided in a filtrate passage extending generally parallel to the opposite side of the filter, so as to create a corresponding pressure drop in the flow direction in the filtrate passage, whereby the pressure difference between both sides of the filter is maintained substantially constant throughout the entire filter area.

7 Claims, 6 Drawing Figures

FILTERING PROCESS

The present invention relates to a filtering process, especially for ultra-filtration, in which a filterable fluid is caused to flow under pressure through a filtering passage extending along one side of a filter, in such a way that a considerable pressure drop arises along the filter area in the flow direction.

In filtering processes of this kind, the pressure on the outlet side of the filter (i.e., the filtrate side) is generally equal throughout the entire filter area, and normally it is equal to the atmospheric pressure. Thus, since the pressure on one side of the filter varies in the flow direction and on the other side thereof is constant, it is easily understood that the pressure difference between the two sides of the filter, i.e., the driving pressure, is different at different parts of the filter area. This causes a number of drawbacks.

First, the risk of filter damage is great in case the filtrate outlet should be shut off. When this happens, the pressure on the filtrate side of the filter rises rapidly to a value which essentially corresponds to the average pressure in the filtering passage. Since the pressure in the part of the filtering passage situated adjacent the outlet is lower than this average pressure, due to the above-mentioned pressure drop, an inverted pressure difference (as compared to normal operation) arises across the filter in the half thereof which is nearest to the outlet. This inverted pressure difference tends to lift said half part of the filter from its support, whereby the filter might easily rupture or be damaged otherwise.

Another drawback of the varying pressure in the filtering passage is that the operational conditions of the filter vary along the entire length thereof, which means that the pressure over a large portion of the filter area will differ considerably from an optimal driving pressure.

A further drawback is that it is impossible to keep the filtrate flow constant by controlling the driving pressure. With a driving pressure exceeding a certain level, the filtrate flow is essentially independent of the driving pressure in normal operation, and therefore a reduced filtrate flow caused by an initial clogging of the filter cannot be compensated for by increasing the driving pressure. Since the driving pressure varies along the filter surface, it is impossible in practice to obtain a driving pressure which at least over the larger portion of the filter area is below the mentioned level. It is thus considered to be inherent in the nature of ultra-filtration that the capacity is uncontrollable.

Furthermore, the cleaning of the filter is made more difficult by the relatively high pressure in the beginning of the filtering passage. The reason for this is that impurities suspended in the cleaning liquid tend to deposit in the mentioned portion of the filter, since the through-flow of liquid is larger there due to the higher driving pressure. The cleaning liquid is of such a nature that it has considerably greater penetrating ability, and unlike the above-mentioned condition in normal operation, the flow through the filter during cleaning is related to the driving pressure.

In accordance with the present invention, the above drawbacks have been eliminated by a filtering process which makes it possible to obtain a driving pressure which is constant throughout the entire filter, in spite of the fact that the mentioned pressure drop causes the pressure in the filtering passage to decrease along the filter. The process is generally characterized in that a fluid flow is provided in the same direction in a filtrate passage extending generally in parallel with the opposite side of the filter (i.e., the filtrate side) so that a corresponding pressure drop arises in the flow direction in the filtrate passage, whereby the pressure difference between both sides of the filter is maintained generally constant throughout the entire filter area.

The invention will be described in more detail below with reference to the accompanying drawings, in which FIGS. 1 through 6 illustrate different embodiments of the invention schematically. The same designations have been used for corresponding means in all the figures.

The ultra-filtering apparatus shown in FIG. 1 has a filtering passage 1 and a filtrate passage 2 which are separated by means of a filter 3. The filterable fluid enters the filtering passage via an inlet conduit 4 and a pump 5 and is discharged via an outlet conduit 6. The latter is connected to the inlet conduit 4 by means of a return conduit 7. By means of the pump 5, a suitable flow velocity is maintained in the filtering passage 1, whereby too rapid clogging of the filter is avoided, a portion of the filtered fluid being returned via the return conduit 7 to the pump 5 to pass through the filtering passage once again.

The filtrate passing through the filter 3 is discharged via an outlet conduit 8 which is provided with a valve 9. By means of a return conduit 10 and a pump 11, a portion of the filtrate is recirculated through the filtrate passage 2. A suitable flow velocity is thus maintained through the filtrate passage, so that a pressure drop of the same magnitude as that in the filtering passage 1 is achieved. The filtrate passage 2 preferably offers a greater hydraulic resistance than that of the passage 1, whereby the demand for capacity of the pump 11 is delimited.

Since the pressure drop in passages 1 and 2 is the same, the driving pressure across the filter will be constant throughout the filter area. This makes it possible to use a driving pressure which is below the mentioned level above which the filtrate flow is independent of the driving pressure. This, in turn, enables the filtrate flow to be controlled by changing the driving pressure, whereby the filtrate flow can be kept constant, if desired. In this way, a successive clogging of the filter tending to reduce the flow therethrough can be compensated for by successively raising the driving pressure to the above-mentioned level. The driving pressure can be varied by controlling the capacity of the pump 5 or by throttling the filtrate flow to a desired value by means of the valve 9. When it becomes impossible to maintain a constant filtrate flow by increasing the capacity of the pump or decreasing the throttling of the filtrate flow by means of the valve 9, which indicates that the mentioned level has been exceeded, the operation must be interrupted and the filter cleaned.

Since the driving pressure is constant throughout the filter area, there is no risk of causing damage or unnormal stress to the filter in case the valve 9 should be closed completely. Furthermore, the operational conditions are the same throughout the entire filter area, which makes it possible to use an optimal driving pressure. Another advantage is that it is possible to use a higher initial pressure in the filtering passage without causing the driving pressure across the portion of the filter adjacent the inlet to increase unacceptably. Also, efficient cleaning is facilitated in that the driving pressure can be maintained at an optional, low level throughout the entire filter area during the cleaning operation, which ensures an equal cleaning of the entire filter.

Figure 2:
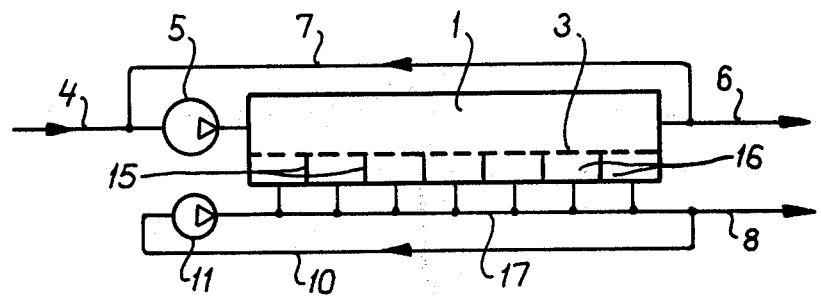

In FIG. 2, the filtrate passage is divided by a plurality of separation walls 15 into a series of chambers 16, each of which is connected to a tube manifold 17. In the latter, a flow with a suitable pressure drop is maintained by means of the pump 11. In this case, the pressure in each of the chamber 16 will be essentially equal to the pressure in the point of the manifold 17 at which the respective chamber is connected. As is easily understood, a gradually decreasing pressure is thereby obtained on the filtrate side of the filter.

Figure 3:
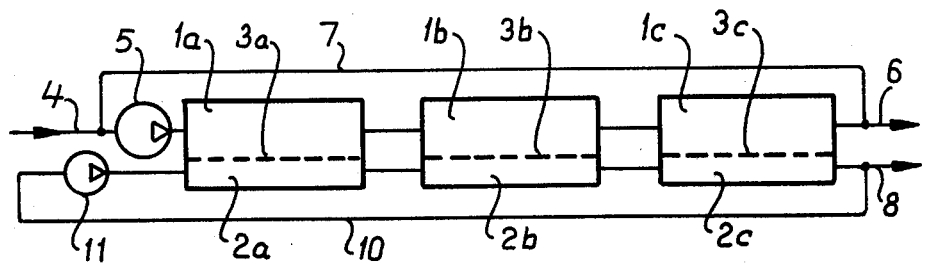

Illustrated in FIG. 3 is a filter system comprising three filtering devices according to FIG. 1 connected in series. To obtain a sufficient driving pressure across the last filter 3c in the series, a relatively high initial pressure is required in the first filtering passage 1a at the inlet from the pump 5. Since this pressure is compensated for by the pressure in the filtrate passages 2a–c, the driving pressure can still be kept constant throughout all the three filters 3a–c.

Figure 4:
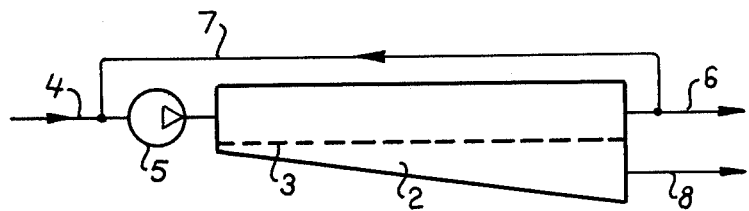

In the embodiment according to FIG. 4, the pump for circulating the filtrate has been omitted and instead the filtrate passage 2 is shaped to have a cross-sectional area which increases in the flow direction. Owing to this shape of the filtrate passage, a pressure is obtained therein which decreases in the direction of the flow. One condition for proper functioning of this embodiment, however, is that a prescribed flow must be maintained in the filtrate passage.

Figure 5:
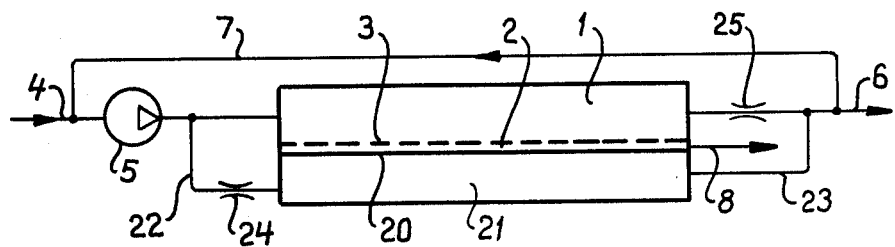

In the embodiment of FIG. 5, a flexible membrane 20 (e.g., of rubber) is provided below the filter 3, the filtrate passage being formed between this membrane and the filter. On the opposite side of membrane 20 a flow with pressure drop is maintained in a passage 21 through which a portion of the fluid supplied by the pump 5 is conducted via conduits 22 and 23. By means of throttle valves 24 and 25 provided in the inlet conduit 22 of the passage 21 and in the outlet conduit of the filtering passage 1, respectively, a suitable ratio between the flows passing through the passages 1 and 21, respectively, is maintained, whereby an appropriate driving pressure across the filter is achieved. The pressure in the passage 21 is transmitted via the membrane 20 to the filtrate passage 2. Thus, the membrane will adjust itself in different positions in relation to the pressures acting on opposite sides thereof, whereby an automatic control of the dimension and shape of the filtrate passage is achieved.

Figure 6:
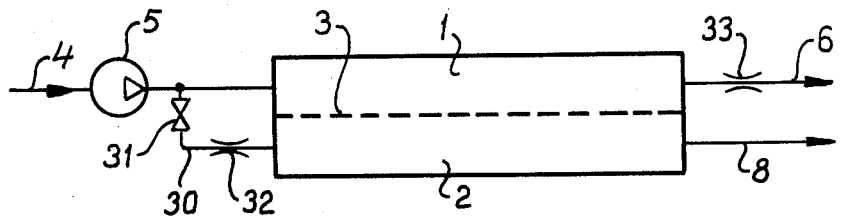

In FIG. 6 is illustrated a simplified embodiment which is intended to keep the driving pressure down during cleaning of the membrane. The filtrate passage 2 is connected to the inlet conduit 4 via a conduit 30 provided with a shut-off valve 31 and a throttle valve 32. During cleaning of the filter, the valve 31 is opened, whereby a portion of the cleaning liquid is conducted via the conduit 30 to the filtrate passage. The flow and the pressure in the filtering passage 1 and the filtrate passage 2 are controlled by suitable adjustment of the throttle valve 32 and an additional throttle valve 33 provided in the outlet conduit 6, whereby an appropriate driving pressure is achieved across the filter 3.

I claim:

1. A filtering process, especially for ultra-filtration, which comprises flowing a filterable fluid under pressure through a filtering passage extending along one side of a filter, passing one part of said fluid through the filter while discharging an unfiltered part of said fluid from an outlet of said passage, said flow through the filtering passage being provided with a sufficiently high velocity to create a substantial pressure drop along the filter area in the flow direction through said passage, providing a fluid flow in the same said direction in a filtrate passage extending generally parallel to the opposite side of said filter, said passage communicating with each other through the filter, and maintaining in said filtrate passage a pressure drop of the same magnitude and in the same direction as said substantial pressure drop in the filtering passage, whereby the pressure difference between both sides of the filter is maintained substantially constant throughout the entire filter area.

2. The process of claim 1, in which the flow through said filtrate passage is provided by returning thereto a portion of the filtrate discharged from said filtrate passage.

3. The process of claim 1, in which the fluid flow through said filtrate passage is passed along the surface of the filter at said opposite side of the filter.

4. The process of claim 1, in which the fluid flow through said filtrate passage is provided through a path spaced from the filter, the filtrate from said opposite side of the filter being directed into a series of separate filtrate chambers adjacent said opposite side and thence into different respective points spaced along the length of said path, a portion of the filtrate from the outlet end of the filtrate passage being returned to the filtrate passage at an inlet end thereof.

5. The process of claim 1, in which said filtrate passage is a filtrate outlet chamber having a cross-sectional area which increases in the flow direction therethrough.

6. The process of claim 1, in which the pressure drop in said filtrate passage is controlled by a flexible membrane separating said filtrate passage from a third passage through which filterable fluid is passed in the same direction as said flow direction through the filtering passage.

7. The process of claim 1, in which at least part of said unfiltered part of the filterable fluid is returned to the filtering passage for repeated flow along the said one side of the filter.

* * * * *